(12) United States Patent
Liu et al.

(10) Patent No.: US 11,564,755 B1
(45) Date of Patent: Jan. 31, 2023

(54) AUTOMATIC KNIFE STOP DEVICE AND SYSTEM FOR FIBULA CUTTING, COMPUTER EQUIPMENT, AND MEDIUM

(71) Applicant: SHANGHAI NINTH PEOPLE'S HOSPITAL, SHANGHAI JIAOTONG UNIVERSITY SCHOOL OF MEDICINE, Shanghai (CN)

(72) Inventors: Jiannan Liu, Shanghai (CN); Junlei Hu, Shanghai (CN); Jing Han, Shanghai (CN); Chenping Zhang, Shanghai (CN); Zilin Wang, Shanghai (CN); Zhiyong Guo, Shanghai (CN); Yige Liu, Shanghai (CN)

(73) Assignee: SHANGHAI NINTH PEOPLE'S HOSPITAL, SHANGHAI JIAOTONG UNIVERSITY SCHOOL OF MEDICINE, Shanghai (CN)

(*) Notice: Subject to any disclaimer, the term of this patent is extended or adjusted under 35 U.S.C. 154(b) by 0 days.

(21) Appl. No.: 17/861,971

(22) Filed: Jul. 11, 2022

(30) Foreign Application Priority Data

Jul. 13, 2021 (CN) .......................... 202110791237.6

(51) Int. Cl.
*A61B 34/10* (2016.01)
*A61B 34/20* (2016.01)

(52) U.S. Cl.
CPC .............. *A61B 34/20* (2016.02); *A61B 34/10* (2016.02); *A61B 2034/108* (2016.02)

(58) Field of Classification Search
None
See application file for complete search history.

(56) References Cited

U.S. PATENT DOCUMENTS

| 2016/0213384 A1 | 7/2016 | Fallin et al. |
| 2022/0265355 A1* | 8/2022 | Ferrante ................. A61B 34/30 |

FOREIGN PATENT DOCUMENTS

| CN | 103961153 | 8/2014 |
| CN | 203915010 | 11/2014 |
| CN | 104825235 | 8/2015 |
| CN | 105997244 | 10/2016 |
| CN | 107951538 | 4/2018 |
| CN | 111481281 | 8/2020 |
| CN | 111772727 | 10/2020 |
| CN | 112370163 | 2/2021 |
| CN | 113034558 | 6/2021 |

* cited by examiner

*Primary Examiner* — Samuel S Hanna
(74) *Attorney, Agent, or Firm* — Global IP Services; Tianhua Gu

(57) ABSTRACT

The present application provides an automatic knife stop device and a system for fibula cutting, a computer equipment, and a medium. The device includes: an acquisition module; a threshold module; and a judgment module. The present application can avoid the destruction of blood vessels during shaping and greatly improve the success rate of surgery, while greatly improve the robustness of the control system by increasing the strength of the force feedback signal.

5 Claims, 4 Drawing Sheets

AUTOMATIC KNIFE STOP DEVICE AND SYSTEM FOR FIBULA CUTTING, COMPUTER EQUIPMENT, AND MEDIUM

CROSS REFERENCE TO RELATED APPLICATION

The present application claims the benefit of priority to Chinese Patent Application No. CN 202110791237.6, entitled "AUTOMATIC KNIFE STOP DEVICE AND SYSTEM FOR FIBULA CUTTING, COMPUTER EQUIPMENT, AND MEDIUM", filed with CNIPA on Jul. 13, 2021, the disclosure of which is incorporated herein by reference in its entirety for all purposes.

FIELD OF TECHNOLOGY

The present disclosure relates to the field of control system, in particular, to an automatic knife stop device and system for fibula cutting, a computer equipment, and a medium.

BACKGROUND

In the reconstruction of a vascularized fibular flap, since the accompanying blood vessels of the fibula are located on the inner side of the fibula and are about 3-5 mm away from the fibula, when the fibular flap is incised, the knife must be stopped immediately to avoid the blade contacting the vessels and ensure that the vessels are not damaged. Due to the characteristics of precision and stability, surgical robots have become one of the means to assist doctors in completing vascularized fibular flap shaping. The surgical robot precisely locates the preoperatively planned position and cuts the fibula. Most of traditional surgical robots use an optical navigation locator to control the position in the osteotomy process, where the surgical accuracies (the error between the length of the cut fibula segment and the corresponding fibula segment designed by surgical planning) are 3.7±2.0 mm and 1.36±0.4 mm. From the perspective of positioning accuracy, the surgical robot guided by the optical positioning system has the risk of damaging the blood vessels. Moreover, there is almost no research related to automatic stop of robotic osteotomy at present.

SUMMARY

The present disclosure provides an automatic knife stop device and a system for fibula cutting, a computer equipment, and a medium, which reduces the risk of damaging blood vessels when cutting fibula that exists with surgical robots guided by conventional optical positioning systems.

The automatic knife stop device for fibula cutting includes an acquisition module, a threshold module, and a judgment module. The acquisition module determines a diameter of the fibula according to preoperative medical images and a preoperative planning scheme, records initial cutting positions respectively, as well as a current cutting position and a corresponding current cutting force in real-time during the cutting process according to the preoperative planning scheme, and continuously updates a maximum cutting force during the cutting process. The threshold module determines a real-time dynamic cutting threshold based on the cutting force curve, the current cutting position, the current cutting force, the diameter of the fibula and the maximum cutting force during the cutting process according to the preoperative planning scheme. The judgment module judges whether the ratio of the current cutting force to the maximum cutting force is greater than the current cutting threshold; if the ratio is not greater than the current cutting threshold, the cutting is continued according to the preoperative planning scheme; if the ratio is greater than the current cutting threshold, the judgment module judge whether the distance from the current cutting position to the initial cutting position is greater than the value of the diameter of the fibula multiplied by a preset coefficient, and if the distance is greater than the value, the judgment module sends a stop command to a cutting saw to stop cutting.

In an embodiment of the present application, the cutting threshold can be obtained by the following method: obtaining an entry point position of the fibula where the cutting saw contacts according to the characteristics of the cutting force curve that the cutting force will rapidly increase from 0 when the cutting saw contacts the fibula, and the cutting force will rapidly decrease when the fibula is broken by the cutting saw;

$$X_T = \mathrm{argmin}\left(\int_0^X F(x)dx + \int_{X+D}^\infty F(x)dx\right);$$

where $X_T$ represents the entry point position of the fibula where the cutting saw actually contacts; $F(x)$ represents the cutting force curve; $X$ represents the current position; $D$ represents the diameter of the fibula; then the cutting threshold is obtained based on $$X_T:T = \frac{F(X_T + D)}{F_{max}},$$

where $T$ represents the cutting threshold, $F_{max}$ represents the maximum cutting force.

In an embodiment of the present application, the current cutting force is obtained through force feedbacks in a plurality of different directions obtained by a plurality of force sensors set on fibula fixtures during the cutting process; the fibula is clamped by the fibula fixtures and remains motionless during the cutting process.

In an embodiment of the present application, a gravity compensation is performed based on the weight of the fibula before obtaining the current cutting force according to the force feedbacks in the plurality of different directions.

In an embodiment of the present application, the current cutting force can be obtained by:

$$F_C = -\sum_{i=1}^n F_i;$$

where the $F_c$ represents the current cutting force, $F_i$ represents the force feedbacks in different positions, n represents the number of the force feedbacks.

In an embodiment of the present application, the preset coefficient less than 1.

The present application provides an computer equipment, which includes a memory, a processor and a communicator; the memory is used for storing computer commands; the processor is used for running the computer commands to realize the functions of the automatic cutter stop device for fibula cutting; the communicator is used for communicating with a cutting saw to send the stop command for cutting, and used for communicating with a fibula fixture to obtain the current cutting force provided by which.

The present application provides an automatic knife stop system for fibula cutting, which includes: the above-described computer equipment; a cutting saw, communicating with the computer equipment for cutting the fibula, and stopping cutting when receiving a stop command sent by the computer equipment; a fibula fixture, communicating with the computer equipment for clamping the fibula, provided with a plurality of force sensors to feed back the cutting force in the cutting process to the computer equipment in real-time according to the principle of reaction force.

The present application provides a computer-readable storage medium with computer instructions that perform the functions of the automatic cutter stop device for fibula cutting as described above when run.

The present application provides an automatic knife stop device, a computer equipment, a system and a medium for fibula cutting, where the automatic knife stop device includes: an acquisition module, used for determining the diameter of the fibula according to the preoperative medical images and the preoperative planning scheme, recording the initial cutting positions respectively, as well as the current cutting position and the corresponding current cutting force in real-time during the cutting process according to the preoperative planning scheme, and continuously updating the maximum cutting force during the cutting process; a threshold module, used for determining the real-time dynamic cutting threshold based on the cutting force curve, the current cutting position, the current cutting force, the diameter of the fibula and the maximum cutting force during the cutting process according to the preoperative planning scheme; a judgment module, used for judging whether the ratio of the current cutting force to the maximum cutting force is greater than the current cutting threshold; if the ratio is not greater than the current cutting, the cutting is continued according to the preoperative planning scheme; if the ratio is greater than the current cutting threshold, the judgment module judges whether the distance from the current cutting position to the initial cutting position is greater than the value of the diameter of the fibula multiplied by a preset coefficient, and if the distance is greater than the value, the judgment module sends a stop command to the cutting saw to stop cutting.

The present disclosure has the following beneficial effects:

The technical solution for automatically stopping the operation of fibula shaping provided in the present application can avoid the destruction of blood vessels during shaping and greatly improve the success rate of surgery, while greatly improve the robustness of the control system by increasing the strength of the force feedback signal.

DETAILED DESCRIPTION

Figure 1:
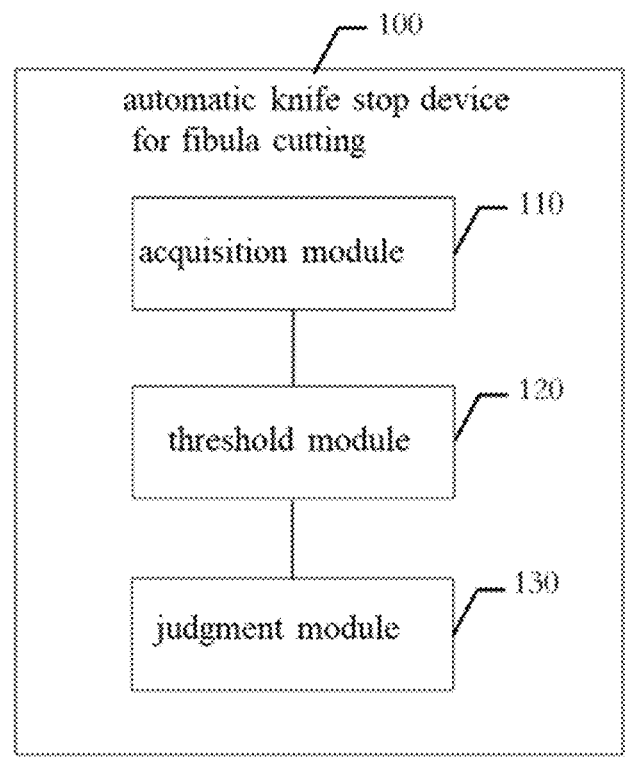
FIG. 1 shows a schematic block diagram of an automatic knife stop device for fibula cutting according to an embodiment of the present application.

The embodiments of the present application are described below through specific examples, and those skilled in the art can easily understand other advantages and effects of the present application from the contents disclosed in this specification. The present application can also be implemented or applied through other different specific embodiments, and various details in this specification can also be modified or changed based on different ideas and applications without departing from the spirit of the present application. It should be noted that the following embodiments and features in the embodiments may be combined with each other under the condition of no conflict.

It should be noted that the drawings provided in the following embodiments are only used to illustrate the basic concept of the present application, and are only shows the elements related to the present application and not necessarily drawn to scale. The type, quantity and proportion of each element can be arbitrarily changed in actual implementation, and the element layout may also be more complicated.

Throughout the specification, the case that a certain part is "connected" to another part includes not only the case of "direct connection", but also the case of "indirect connection" with other elements interposed therebetween. In addition, when a certain part "includes/comprises" a certain element, unless otherwise specified, it does not mean to exclude other elements, but means that other constituent elements may also be included.

The terms first, second, and third mentioned herein are used for the purpose of describing various parts, components, regions, layers and/or sections and are not intended to be limited. These terms are only used to distinguish one part, component, region, layer or section from those of another. Thus, a first part, component, region, layer or section below may refer to a second part, component, region, layer or section without departing from the scope of the present application.

Also, as used herein, the singular forms "a," "an," and "the" are intended to include the plural forms as well, unless otherwise specified. It should be further understood that the terms "comprising", "including" indicate the presence of stated features, operations, elements, components, items, categories, and/or groups, but do not exclude the existence, appearance or addition of one or more of other features, operations, elements, components, items, categories, and/or groups. The terms "or" and "and/or" as used herein are to be construed to be inclusive or to mean any one or any combination. Thus, "A, B or C" or "A, B and/or C" means "any of the following: A; B; C; A and B; A and C; B and C; A, B and C". Exceptions to this definition arise only when combinations of elements, functions, or operations are inherently mutually exclusive in some way.

To decrease the risk of destroying blood vessels when a surgical robot guided by optical positioning system cuts the fibula, the present application provides an automatic knife stop device for fibula cutting.

FIG. 1 shows a schematic block diagram of an automatic knife stop device for fibula cutting according to an embodiment of the present application. The device 100 includes an acquisition module 110, a threshold module 120, and a judgment module 130.

The acquisition module 110 determines a diameter of the fibula according to preoperative medical images and a preoperative planning scheme, records initial cutting positions respectively, as well as a current cutting position and a corresponding current cutting force in real-time during the cutting process according to the preoperative planning scheme, and continuously updates a maximum cutting force during the cutting process.

To put it simply, to cut the fibula, the preoperative medical images will be taken first, and the preoperative planning will be schemed. In the actual process of cutting the fibula, the fibula is also connected with blood vessels and muscle tissue, so the complete cutting process also includes the cutting for non-bone part of the tissue; in addition, the diameter of the fibula in this application is not the maximum diameter or the average diameter of the fibula, but corresponds to the cutting path in the preoperative planning scheme. Since the fibula is not a cylinder, its actual cutting path corresponds to the diameter of the fibula in this application.

Therefore, the present application obtains the diameter of the fibula based on the clear fibula tissue area in the preoperative medical images, combined with the actual cutting path in the preoperative planning scheme.

Preferably, the initial cutting position described in the present application corresponds to the initial position in the preoperative planning scheme, that is, the position is mostly located in muscle tissue rather than fibula structure.

In an embodiment of the present application, the current cutting force is obtained through the force feedbacks in a plurality of different directions obtained by a plurality of force sensors set on fibula fixtures during the cutting process; the fibula is clamped by the fibula fixtures and remains motionless during the cutting process.

Preferably, the force sensors are strain gauges, so as to be respectively arranged on supporting structures of different dimensions.

It should be noted that the fibula fixture of the present application is not limited to a specific structure. But preferably, the fibula fixture has a three-dimensional support structure, so as to be arranged on structures of multiple dimensions and obtain force feedbacks from the multiple directions.

Figure 2:
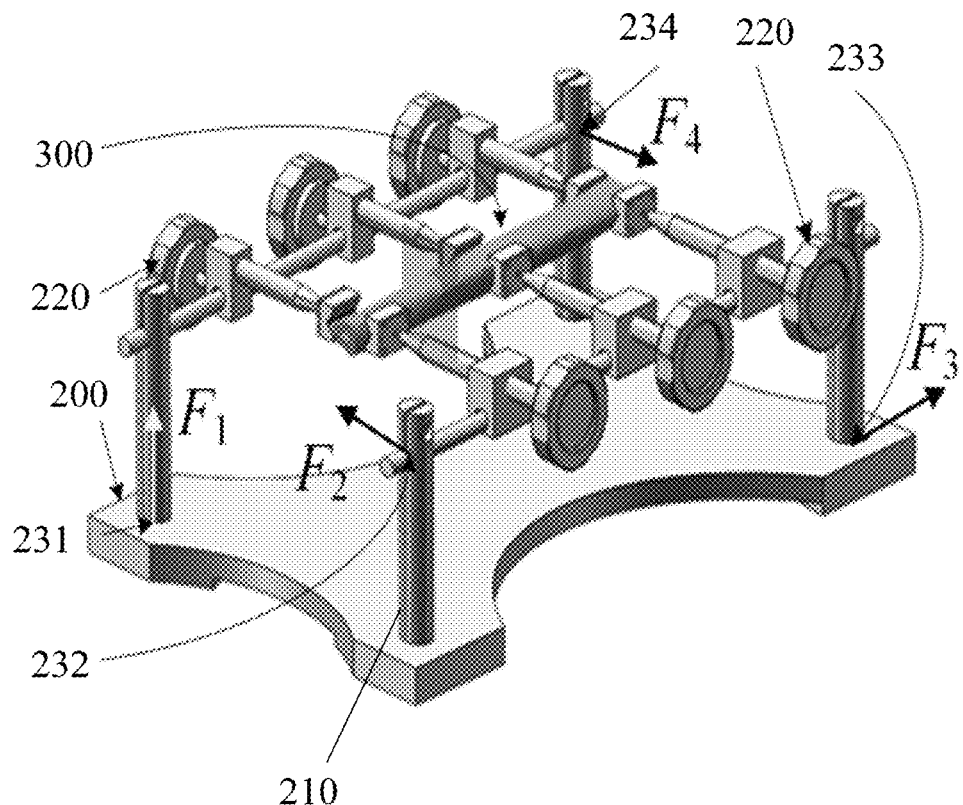
FIG. 2 shows a schematic structural diagram of a fibula fixture in an embodiment of the present application.

FIG. 2 is a schematic structural diagram of a fibula fixture in real-time of the present application. As shown in the figure, the fibula fixture 200 includes four support frames 210, a plurality of adjustable clamping mechanisms 220 are disposed on the adjustable clamping mechanisms 220 for clamping the fibula 300. Specifically, force sensors can be set at positions 231-234 to obtain force feedbacks F1-F4 in a plurality of directions. Preferably, the three directions of F1, F2, and F3 are perpendicular to each other, and the directions of F2 and F4 are opposite to each other.

In the present application, the current cutting force can be directly calculated by a processor provided on the fibula fixture, and the calculated numerical parameters of the current cutting force can be sent to the acquisition module 110 of the device 100; alternatively, the fibula fixture only transmits force feedback data in the plurality of different directions to the acquisition module 110 of the device 100, and the acquisition module 110 calculates the current cutting force through the corresponding direction or angle.

In an embodiment of the present application, a gravity compensation is performed based on the weight of the fibula before obtaining the current cutting force according to the force feedbacks in the plurality of different directions. Therefore, after the gravity compensation, according to the principle of force and reaction force, the current cutting force can be calculated:

$$F_C = -\sum_{i=1}^{n} F_i;$$

Where $F_c$ represents the current cutting force; $F_t$ represents the force feedbacks in different positions, n represents the number of the force feedbacks or the force sensors.

For example, as shown in FIG. 2, 4 force sensors are placed in the fibula fixture, then n=4.

The threshold module 120 determines a real-time dynamic cutting threshold based on the cutting force curve, the current cutting position, the current cutting force, the diameter of the fibula and the maximum cutting force during the cutting process according to the preoperative planning scheme.

Figure 3:
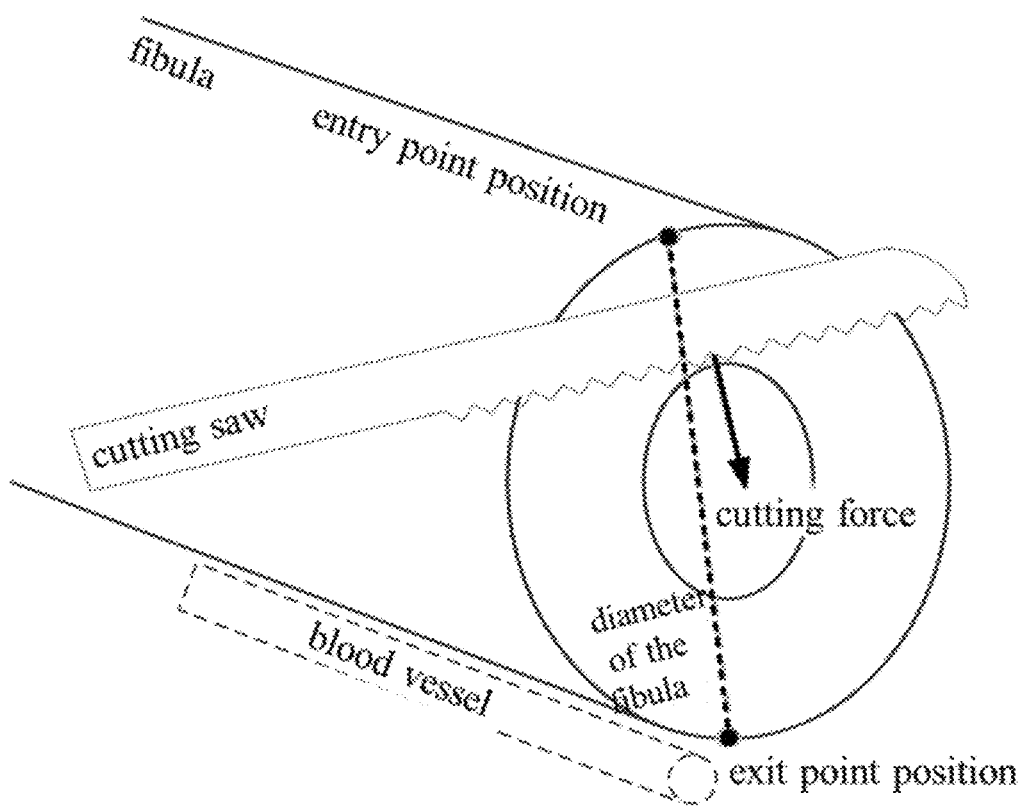
FIG. 3 shows a schematic scene diagram of fibula cutting in an embodiment of the present application.

FIG. 3 shows a schematic scene diagram of fibula cutting in an embodiment of the present application.

Figure 4:
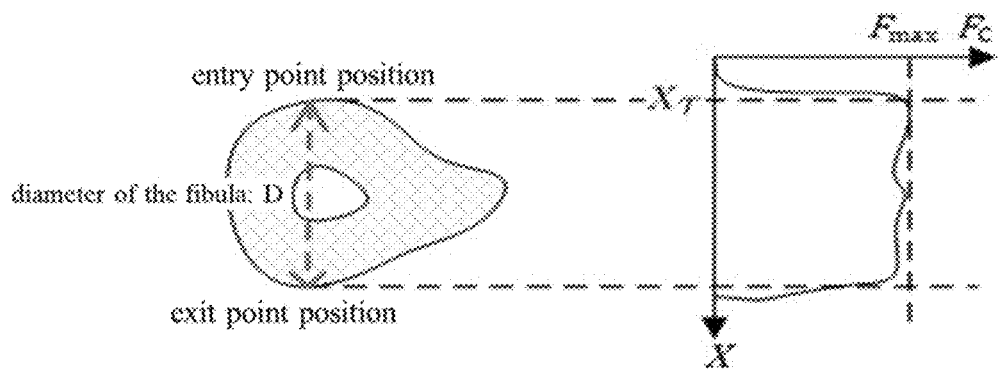
FIG. 4 shows a schematic model diagram of the variation of cutting force in an embodiment of the present application.

FIG. 4 shows a schematic model diagram of the variation of cutting force. The right side of the figure shows a curve of the cutting force $F_c$ changing with a displacement X, wherein $F_{max}$ represents the maximum cutting force during the cutting process. In a cutting process, the cutting force will rapidly increase from 0 when the cutting saw contacts the fibula, and the cutting force will rapidly decrease when the fibula is broken by the cutting saw. In order to judge whether the fibula is broken, a cutting threshold is used in this application:

Firstly, according to the characteristic of the cutting force curve that the cutting force will increase rapidly from 0 when the cutting saw contacts the fibula, and the cutting force will rapidly decrease when the fibula is broken by the cutting saw, calculating an entry point position of the fibula where the cutting saw actually contacts:

$$X_T = \mathrm{argmin}\left( \int_0^X F(x)dx + \int_{X+D}^{\infty} F(x)dx \right).$$

Where $X_T$ represents the entry point position of the fibula where the cutting saw actually contacts; F(x) represents the cutting force curve; X represents the current position; D represents the diameter of the fibula.

Specifically, $$\int_0^X F(x)dx$$

represents the change interval of the cutting force of the cutting saw from the time when the cutting saw starts to move until the cutting saw contacts the fibula, $$\int_{X+D}^{\infty} F(x)dx$$

represents the change interval of the cutting force of the cutting saw from the time when the cutting saw leaves the fibula until the cutting saw stops moving. The minimum value of the position X between the above two intervals is obtained through the argmin function, the position X is the entry point position which actually contacts fibula, so as to obtain the entry point position $X_T$.

Then the cutting threshold is obtained based on:

$$T = \frac{F(X_T + D)}{F_{max}}.$$

Where T represents the cutting threshold, $F_{max}$ represents the maximum cutting force.

The cutting threshold in the present application can be obtained by calculating the formula above at the beginning of cutting according to the preoperative planning scheme. Therefore, the cutting threshold can be obtained at the beginning of the cutting process. And since the maximum cutting force $F_{max}$ in this application is continuously updated during the cutting process, therefore, referring to the cutting force curve shown in FIG. 4, it can be seen that the maximum cutting force $F_{max}$ is dynamic between the origin and the entry point position $X_T$, and the maximum cutting force $F_{max}$ after the entry point position $X_T$ is not greater than the maximum cutting force at the entry point position $X_T$. Therefore, after reaching the entry point position $X_T$, the cutting threshold T does not change any more.

The judgment module 130 judges whether the ratio of the current cutting force to the maximum cutting force is greater than the current cutting threshold; if the ratio is not greater than the current cutting threshold, the cutting is continued according to the preoperative planning scheme; if the ratio is greater than the current cutting threshold, judge whether the distance from the current cutting position to the initial cutting position is greater than the value of the diameter of the fibula multiplied by a preset coefficient, and if so, send a stop command to the cutting saw to stop cutting.

Figure 5:
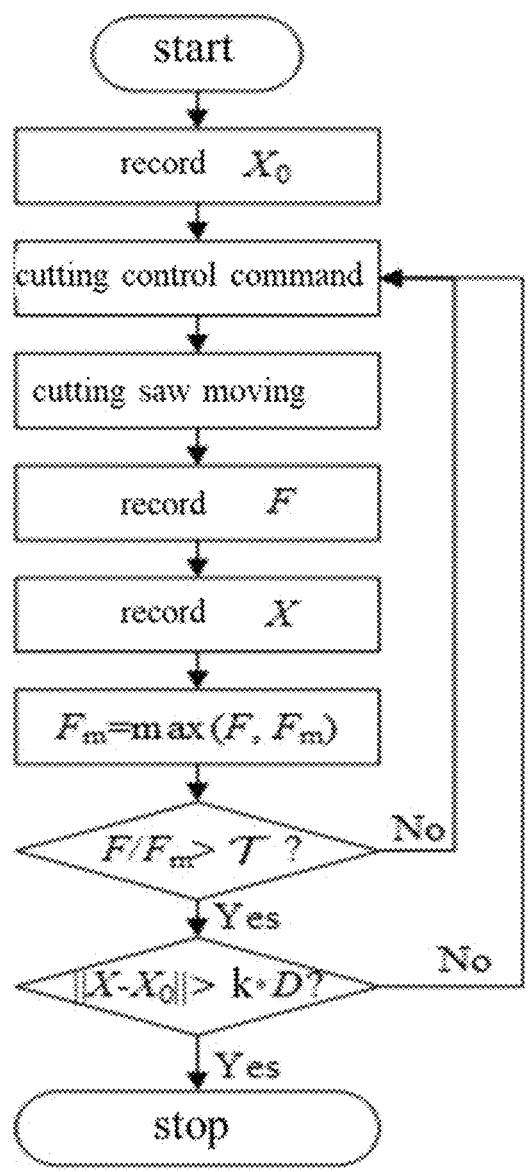
FIG. 5 shows a schematic flowchart of determination control in an embodiment of the present application.

FIG. 5 shows a schematic flowchart of determination control. For example, after starting, first record the initial cutting position $F_0$, and then issue a cutting control command to allow the cutting saw start to move or work, and simultaneously record the current cutting force F and the current cutting position X, and the maximum cutting force $F_{max}$ is continuously updated during the cutting process. If the value of $F/F_{max}$ is not greater than the cutting threshold L; the cutting is continued according to the preoperative planning scheme; otherwise, judge whether the distance from the current cutting position F to the initial cutting position $F_0$ is greater than the value of k*D, and if the distance is greater than the value of k*D, command the robot to stop the cutting.

For example, the preset coefficient k is less than 1, such as 0.8, 0.9, etc. the purpose of k*D is to ensure that the distance from the current cutting position to the initial cutting position is less than the diameter of the fibula, thereby avoiding a wrong judgment that the cutting of the fibula is completed.

To sum up, the technical solution for automatically stopping the operation of fibula shaping provided in the present application can avoid the destruction of blood vessels during shaping and greatly improve the success rate of surgery, while greatly improve the robustness of the control system by increasing the strength of the force feedback signal.

It should be understood that the division of each module of the above device is only a division of logic function, and may be completely or partially integrated on one physical entity or physically separated in actual implementation.

Besides, these modules can be all implemented in the form of software by processing element calls, also can be implemented in the form of hardware; alternatively, some of modules can be all implemented in the form of software by processing element calls, and others can be implemented in the form of hardware. For example, the judgement module 130 can be a separate processing element or integrated in a certain chip of the above system. In addition, it can also be stored in the memory of the above system in the form of program code, and is called by a certain processing element of the above system to execute the function of the module. Other modules are implemented similarly. In addition, all or part of these modules can be integrated together or implemented independently. The processing element described here can be an integrated circuit with signal processing capabilities. In the implementation process, each step or module of the method may be completed through the integrated logic circuit of hardware in the processing element or through the instruction in the form of software.

For example, the above modules may be one or more integrated circuits configured to implement the above method, the integrated circuits may be one or more Application Specific Integrated Circuits (ASIC), one or more digital signal processors (DSP), or one or more Field Programmable Gate Arrays (FPGA), and the like. For another example, in the case where one of the above modules is implemented in the form of a processing element calling program code, the processing element may be a general-purpose processor, such as a central processing unit (CPU) or other processors that can call program codes. For another example, the above modules can be integrated together and implemented in the form of a system-on-a-chip (SOC).

Figure 6:
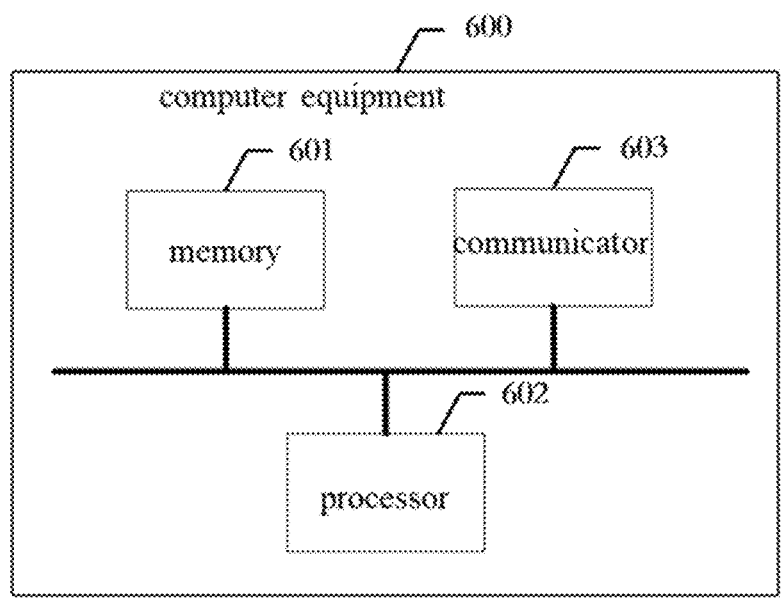
FIG. 6 shows a schematic structural diagram of a computer equipment in an embodiment of the present application.

FIG. 6 shows a schematic structural diagram of a computer equipment in an embodiment of the present application. As shown in the figure, the computer equipment 600 includes a memory 601, a processor 602, and a communicator 603. The memory 601 stores computer instructions; the processor 602 executes the computer instructions to implement the function of the automatic knife stop device for fibula cutting shown in FIG. 1; the communicator 603 communicates with a cutting saw to send a stop command to the cutting saw to stop cutting, and communicates with a fibula fixture to obtain the real-time cutting force provided by it.

In an embodiment, the number of the memory 601 in the computer equipment 600 may be one or more, the number of the processor 602 may be one or more, and the number of the communicator 603 may be one or more, and the computer equipment 600 in FIG. 6 takes one as an example.

In an embodiment of the present application, the processor 602 in the computer equipment 600 loads one or more instructions corresponding to the process of an application into the memory 601 according to the steps shown in FIG. 1. The processor 602 runs the application stored in the memory 601, thereby realizing the function of the object detection hardware accelerator.

The memory 601 may include random access memory (RAM for short), and may also include non-volatile memory, such as at least one disk memory. The memory 601 stores an operating system and operation instructions, executable modules or data structures, or their subsets or extended sets, wherein the operation instructions may include various operation instructions for implementing various operations. The operating system may include various system programs for implementing various basic services and handling hardware-based tasks.

The processor 602 may be a general-purpose processor, including a central processing unit (CPU for short), a network processor (NP for short), etc.; or may be a digital signal processor (DSP for short), application specific integrated circuit (ASIC for short), field-programmable gate array (FPGA for short) or other programmable logic devices, discrete gate, transistor logic devices or discrete hardware components.

The communicator 603 is used to realize the communicatively connection between a database access device and other devices (e.g clients, read-write libraries and read-only libraries). The communicator 603 may include one or more groups of modules with different communication modes, for example, a CAN communication module communicatively connected to the CAN bus. The communicatively connection may refer to one or more wired/wireless communication means and combinations thereof. The communication means include: Internet, CAN, intranet, wide area network (WAN), local area network (LAN), wireless network, digital subscriber line (DSL) network, frame relay network, asynchronous transfer mode (ATM) network, virtual private network (VPN) and/or any one or more of other suitable communication networks. For example: any one or a combination of WIFI, Bluetooth, NFC, GPRS, GSM, and Ethernet.

In some specific embodiments, various components of the computer equipment 600 are coupled together through a bus system, where the bus system may include a power bus, a control bus, a status signal bus, and the like in addition to a data bus. However, for the sake of clarity of illustration, the various buses are referred to as bus systems in FIG. 6.

Figure 7:
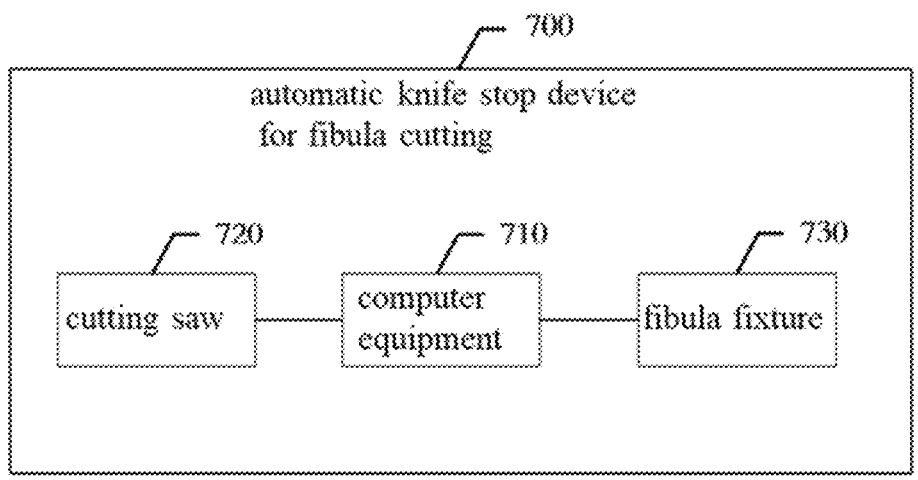
FIG. 7 shows a schematic structural diagram of an automatic knife stop system for fibula cutting in an embodiment of the present application.

FIG. 7 shows a schematic structural diagram of an automatic knife stop system for fibula cutting in an embodiment of the present application. As shown in FIG. 7, the automatic stop system 700 for cutting fibula includes: a computer equipment 710 as described in FIG. 6, a cutting saw 720, and a fibula fixture 730.

The cutting saw 720 communicates with the computer equipment 710 to cut the fibula, and stops cutting when a stop command sent by the computer equipment 710 is received.

The fibula fixture 730 communicates with the computer equipment 710 to clamp the fibula, is provided with a plurality of force sensors to feed back the cutting force during the cutting process to the computer equipment 710 in real time according to the principle of reaction force. Where the fibula fixture 730 may refer to the fibula fixture shown in FIG. 2.

In an embodiment of the present application, the present application provides a computer-readable storage medium on which computer programs are stored, and when the programs are executed by a processor, the computer-readable storage medium realizes the function of the automatic knife stop device for fibula cutting as described in FIG. 1.

The present application may be a system, method and/or computer program product at any possible level of incorporation of technical details. The computer program product may include a computer-readable storage medium on which computer-readable program instructions loaded, to allow a processor to implement various aspects of the present application.

The computer-readable storage medium may be a tangible device that can hold and store instructions for use by an instruction execution device. The computer-readable storage medium may be, for example, but not limited to, an electrical storage device, a magnetic storage device, an optical storage device, an electromagnetic storage device, a semiconductor storage device, or any suitable combination of the above. More specific examples (non-exhaustive list) of the computer readable storage medium include: portable computer disks, hard disks, random access memory (RAM), read only memory (ROM), erasable programmable read only memory (EPROM or flash memory), static random access memory (SRAM), portable compact disk read only memory (CD-ROM), digital versatile disk (DVD), memory sticks, floppy disks, mechanically coded devices, punch cards with instructions stored thereon, raised structures in grooves, or any suitable combination of the above. The computer-readable storage medium, as used herein, are not to be construed as transient signals per se, such as radio waves or other freely propagating electromagnetic waves, or electromagnetic waves propagating through waveguides, other transmission medium (e.g., light pulses of fiber optic cables), or electrical signals transmitted through electrical wires.

The computer-readable programs described herein can be downloaded to various computing/processing devices from the computer-readable storage medium, or to external computers or storage devices over a network such as the Internet, local area network, wide area network, and/or wireless network. The network may include copper transmission cables, fiber optic transmission, wireless transmission, routers, firewalls, switches, gateway computers, and/or edge servers. A network adapter card or network interface in each computing/processing device receives computer-readable program instructions from a network and forwards the computer-readable program instructions for storage in the computer-readable storage medium in each computing/processing device. The computer program instructions for carrying out the operations of the present application may be assembly instructions, instruction set architecture (ISA) instructions, machine instructions, machine-dependent instructions, microcode, firmware instructions, state setting data, integrated circuit configuration data, or, source or object code written in any combination of one or more programming languages, which includes object-oriented programming languages, such as Smalltalk, C++, etc.; and procedural programming languages, such as the "C" language or similar programming languages. The computer readable program instructions may execute entirely or partly on a user's computer, execute as a stand-alone software package, execute partly on a user's computer and partly on a remote computer, or execute entirely on a remote computer or server. In the case of a remote computer, the remote computer may be connected to a user's computer through any kind of network, including a local area network (LAN) or a wide area network (WAN), or may be connected to an external computer (e.g., through the Internet provided by an Internet service provider). In some embodiments, custom electronic circuits, such as programmable logic circuits, field programmable gate arrays (FPGAs), or programmable logic arrays (PLAs), can be personalized by utilizing state information of the computer readable program instructions, to execute the computer readable program instructions to implement various aspects of the present application.

The present application provides an automatic knife stop device and system for fibula cutting, a computer equipment, and a medium. The automatic knife stop device includes: an acquisition module, used for determining the diameter of the fibula according to the preoperative medical images and the preoperative planning scheme, recording the initial cutting positions respectively, as well as the current cutting position and the corresponding current cutting force in real-time during the cutting process according to the preoperative planning scheme, and continuously updating the maximum cutting force during the cutting process; a threshold module, used for determining the real-time dynamic cutting threshold based on the cutting force curve, the current cutting position, the current cutting force, the diameter of the fibula and the maximum cutting force during the cutting process according to the preoperative planning scheme; a judgment module, used for judging whether the ratio of the current cutting force to the maximum cutting force is greater than the current cutting threshold; if the ratio is not greater than the current cutting threshold, the cutting is continued according to the preoperative planning scheme; if the ratio is greater than the current cutting threshold, the judgment module judges whether the distance from the current cutting position to the initial cutting position is greater than the value of the diameter of the fibula multiplied by a preset coefficient, and if the distance is greater than the value, the judgment module sends a stop command to the cutting saw to stop cutting.

The present application effectively overcomes various shortcomings in the prior art and has high industrial application value.

The above-mentioned embodiments merely illustrate the principles and effects of the present application, but are not intended to limit the present disclosure. Anyone skilled in the art can make modifications or changes to the above embodiments without departing from the spirit and scope of the present application. Therefore, all equivalent modifications or changes made by persons of ordinary skill in the technical field without departing from the spirit and technical idea disclosed in the present disclosure shall still be covered by the claims of the present application.

What is claimed is:

1. An automatic cutting saw stop system for a fibula cutting, comprising:
   a cutting saw;
   a fibula fixture;
   a plurality of force sensors;
   an acquisition module, a threshold module, and a judgment module; and
   a computer equipment comprising: a memory, a processor and a communicator, computer instructions stored in the memory; the processor executes the computer instructions to:
   (i) communicate with the acquisition module to determine a diameter of the fibula according to preoperative medical images and a preoperative planning scheme, record initial cutting positions of the fibula respectively, as well as a current cutting position of the saw and a corresponding current cutting force applied by the saw in real-time during a cutting process according to the preoperative planning scheme, and continuously update a maximum cutting force applied by the saw during the cutting process;
   (ii) communicate with the threshold module to determine a real-time dynamic cutting threshold based on a cutting force curve, the current cutting position of the saw, the current cutting force applied by the saw, the diameter of the fibula, and the maximum cutting force applied by the saw during the cutting process according to the preoperative planning scheme;
   (iii) calculate, using a second mathematical formula, the cutting threshold by: obtaining, using a first mathematical formula, an entry point position of the fibula where the cutting saw contacts according to the characteristics of the cutting force curve that the cutting force will rapidly increase from 0 when the cutting saw contacts the fibula, and the cutting force will rapidly decrease when the fibula is broken by the cutting saw;
   the first mathematical formula used for obtaining the entry point position of the fibula is:

$$X_T = \mathrm{argmin}\left(\int_0^X F(x)dx + \int_{X+D}^{\infty} F(x)dx\right)$$

wherein $X_T$ represents the entry point position of the fibula where the cutting saw actually contacts the fibula; $F(x)$ represents the cutting force curve, $X$ represents the current position of the saw; $D$ represents the diameter of the fibula; obtain the cutting threshold based on the entry point $X_T$, the second mathematical formula used for calculating the cutting threshold is:

$$T = \frac{F(X_T + D)}{F_{max}};$$

wherein $T$ represents the cutting threshold, $F_{max}$ represents the maximum cutting force; and
   (iv) communicate with the judgment module to judge whether a ratio of the current cutting force to the maximum cutting force is greater than the cutting threshold; wherein if the ratio is not greater than the cutting threshold, cutting is continued according to the preoperative planning scheme; wherein if the ratio is greater than the cutting threshold, the judgment module judges whether a distance from the current cutting position to an initial cutting position is greater than a value of the diameter of the fibula multiplied by a preset coefficient, wherein if the distance is greater than the value, the judgment module sends a stop command to the cutting saw to stop cutting;
   the cutting saw communicates with the computer equipment to cut the fibula and stop cutting when receiving the stop command sent by the computer equipment;
   the fibula fixture communicates with the computer equipment to clamp the fibula;
   the plurality of force sensors are configured to be disposed on the fibula to feed back the cutting force in the cutting process to the computer equipment in real-time according to the principle of reaction force; and
   the communicator communicates with the cutting saw to send the stop command to the cutting saw to stop cutting, and communicates with the fibula fixture to obtain a real-time cutting force provided by the fibula fixture.

2. The automatic knife stop device according to claim 1, wherein the current cutting force is obtained through force feedbacks in a plurality of different directions obtained by the plurality of force sensors set on the fibula fixtures during the cutting process; wherein the fibula is configured to be clamped by the fibula fixtures and remains motionless during the cutting process.

3. The automatic knife stop device according to claim 2, wherein a gravity compensation is performed, using the computer equipment, based on a weight of the fibula before obtaining the current cutting force according to the force feedbacks in the plurality of different directions.

4. The automatic knife stop device according to claim 2, wherein the current cutting force is recorded using a third mathematical formula being:

$$F_C = -\sum_{i=1}^{n} F_i;$$

wherein F represents the current cutting force, $F_i$ represents the force feedbacks in different positions, n represents the number of the force feedbacks.

5. The automatic knife stop device according to claim 1, wherein a preset coefficient is less than 1.

* * * * *